United States Patent [19]

O'Neill

[11] Patent Number: 4,543,339
[45] Date of Patent: Sep. 24, 1985

[54] EARLY PREGNANCY DETECTION BY DETECTING ENHANCED BLOOD PLATELET ACTIVATION

[76] Inventor: Christopher O'Neill, Flat 1, 83 St. Johns Rd., Glebe 2037, N.S.W., Australia

[21] Appl. No.: 475,546

[22] Filed: Mar. 15, 1983

[30] Foreign Application Priority Data

Mar. 16, 1982 [AU] Australia ................................ PF3148

[51] Int. Cl.$^4$ ..................... G01N 33/48; G01N 33/50; G01N 33/54
[52] U.S. Cl. .................................... 436/510; 204/403; 435/13; 435/23; 436/63; 436/65; 436/533; 436/814
[58] Field of Search ................... 436/510, 65, 63, 533, 436/814; 435/13

[56] References Cited

U.S. PATENT DOCUMENTS 4,310,455  1/1982  Bahl ................................. 436/510 X
4,419,453  12/1983  Dorman .......................... 436/510 X

OTHER PUBLICATIONS

Chemical Abstracts, 88:20010y, (1978).

Primary Examiner—Sidney Marantz
Attorney, Agent, or Firm—Ladas & Parry

[57] ABSTRACT

A method and reagent system for detecting pregnancy in a mammal at an early stage by detecting enhanced activation of blood platelets.

15 Claims, No Drawings

EARLY PREGNANCY DETECTION BY DETECTING ENHANCED BLOOD PLATELET ACTIVATION

The present invention relates to the detection of pregnancy in mammals (particularly agricultural and domestic animals) at a very early stage. The invention is based on the monitoring of changes in the haemostatic system (i.e. the blood coagulation system).

Traditionally, the diagnosis of pregnancy is based on missed menstrual periods (human) or a failure to return to oestrus (animal species). Depending on the mammal species, this may take from several days to several weeks.

For humans, the most commonly used experimental test for detecting pregnancy is based upon the immunological detection of human chorionic gonadotrophin (HCG). HCG is a glycoprotein hormone produced by the placenta during pregnancy, and may be found in blood and urine samples of pregnant women. The latex particle test for HCG is well known and well established for use with humans. However, the HCG hormone does not appear in conveniently measurable amounts until about 2 or 3 weeks following a missed period. By this time pregnancy, if it exists, can no longer be terminated by menstrual regulation and abortion, if required, must be brought about by more complicated techniques.

In non-human animals, the production of chorionic gonadotrophin does not occur until much later in pregnancy than in humans. The early detection of pregnancy would be an important advantage in monitoring artificial insemination (for example, in cattle) or in the early detection of pregnancy in horse stud farms. At present there is for all practical purposes no test capable of detecting pregnancy at an early stage in such animals e.g. in less than a month following conception.

It has been known for some time that during pregnancy dramatic changes occur in the human haemostatic system. In particular fibrin levels in the blood are enhanced, together with levels of other haemostatic factors. This is believed to be due to the requirements of the placenta and particularly to a need to staunch blood flow during and after placental separation at birth. The overall changes are consistent with the enhanced generation of thrombin. It has normally been possible to detect the effect of pregnancy on the haemostatic system from the third month of pregnancy onwards in humans.

The present invention is based on the unexpected discovery that detectable effects related to changes in platelet activity occur at a very early stage in pregnancy. Indeed, the changes closely follow conception and provide the basis for pregnancy detection at a very early stage.

Thus, the present invention provides a method of detecting pregnancy in a mammal at an early stage, which comprises detecting physiological change consequent on increased activity of blood platelets resulting from the pregnancy.

The invention is applicable to sheep, goats, cattle, pigs, horses, dogs and cats; and to humans.

The haemostatic system is a very complex system of enzymes leading to the production of the enzyme thrombin which controls the production of fibrin. Fibrin is a proteinaceous material effective in building the blood clot. The system comprises a number of enzymes (Factors) which operate in a cascade sequence.

Although fibrin can be generated in the absence of cells, the physiological norm is for the involvement of platelets, also known as thrombocytes. The role of platelets in haemostasis is to form plugs in injured vessels and to provide a phospholipid material that greatly accelerates plasma coagulation. The primary event underlying the function of platelets is their activation from a non-adhesive to an adhesive state in which they adhere both to the substratum and to each other to form aggregates. The activation can be triggered by a multitude of factors, and in turn the efficiency of these factors can be either enhanced or inhibited by numerous other factors.

These factors may be referred to generally as thrombogenic stimuli. In broad terms, this preferred embodiment of the invention depends on differences in reactivity of platelets from pregnant and non-pregnant animals (or platelets exposed to body fluids from pregnant or non-pregnant animals) to the thrombogenic stimuli.

The activation of platelets leads to conversion of the cells from a non-adhesive to an adhesive state resulting in extensive morphological alterations and the excretion of $Ca^{2+}$, phospholipids and other substances. The excreted products assist in the activation of fluid phase coagulation.

It has been found particularly advantageous to detect pregnancy by monitoring activation of platelets.

When the activation of platelets was examined it was found that there was much greater stimulation of platelet transformation from pregnant animals than from non-pregnant animals and similarly with platelets from non-pregnant animals exposed to body fluids of pregnant animals. This enhanced activity can be detected by the first day of pregnancy and, in the mouse at least, it can be detected within twelve hours of fertilization of the ovum.

The extent of activation of the platelets can be monitored by any of many methods known to the skilled man. Such methods might include visualization with microscopy of the extent of morphological change, monitoring the release of excreted factors (such as $Ca^{2+}$, ADP, fibrin, phospholipid, fibronectin, etc.) spectrophotometric detection of the change in optical density of a solution containing platelets; or the determination of the onset of membrane adhesiveness by the ability of the platelets to causae agglutination of latex particles.

The present invention has shown that an early response to pregnancy in mice is a 30-50% decrease in blood platelet count. This occurs within 12 hours of fertilization of the ovum in mice. This decrease does not occur in:

(1) females mated with vasectomized mice,
(2) females rendered infertile by tubal ligation and subsequently mated with fertile males,
(3) in males, or
(4) in females at various stages of the oestrus cycle.

This decrease does occur in both inbred and outbred colonies of mice. The decreased platelet count lasts for at least the first 6 days of pregnancy. It has been shown that this decrease in platelet count is not simply due to the sequestering of platelets by the spleen (spleen platelet count actually decreases in early pregnancy as well) but due to a consumptive thrombocytopenia (i.e. actual consumption of platelets due to platelet activation). Later in pregnancy the platelet count returns close to normal values and this may be due to an increase in platelet production.

This decrease in platelet concentration may in itself be enough to explain the gross changes in blood clotting during pregnancy. Platelet activation and consumption cause the release of many factors from platelet granules. These factors enhance the activation of other platelets and also enhance fluid phase coagulation.

There are two separate, yet interrelated, aspects of platelet activation which can be studied in vitro, there are:

(1) platelet adhesion to foreign surfaces, and
(2) platelet aggregation.

It has been shown according to the invention that both platelet adhesion and platelet aggregation increase during early pregnancy.

Platelet Adhesion

Platelet adhesion is a calcium independent event. The ability of a surface to induce platelet adhesion is dependent upon the total electric charge of the surface and upon the critical surface tension. In general terms, substances with a critical surface tension of greater than 30 dynes/cm and with a low electronegativity value can be considered thrombogenic. The influence of critical surface tension is particularly important where there is very short contact time with the platelets, as is the case in many of the presently proposed assay procedures.

In clinical practice, the most widely used method for the quantification of platelet adhesion is based on the principle that following exposure of blood to a foreign surface the platelet count decreases. This technology requires the packing of a column with glass (or plastic) beads. A volume of anticoagulated blood with known platelet concentration is passed through the column and a platelet count of this blood is subsequently made. The difference in the platelet count is thus a measure of platelet adhesion.

An alternative method which has been developed for pregnancy diognosis is again based on the principle that platelets adhere to foreign surfaces. Blood containing anticoagulants (e.g. sodium citrate) or EDTA, is exposed to a glass or plastic surface for a short period of time (e.g. less than 8 minutes) at room temperature. The excess blood is washed off with a physiological solution (e.g. 0.9% saline, or Ca and Mg free phosphate buffered saline). The remaining adherent platelets are fixed to the surface with any of the well known fixatives, e.g. ethanol, methanol 80-100% or formaldehyde and glutaraldehyde, 2-10% in physiological solution. The humber of fixed platelets are then quantified by a number of known direct or indirect methods.

Direct methods include the visualization and counting of the platelets by microscopy. This can be achieved with phase microscopy, or the visualization of the platelet by staining with any number of histological stains, e.g. Colloidal Iron-Purssion blue, or Alcian Blue.

Indirect methods for quantification of the adherence include the exposure of the adhering platelets to specific labelling substances. The most convenient of these is an appropriately labelled anti-sera. The anti-sera may be a specific anti-platelet anti-sera or a less specific anti-sera recognising species or tissue antigens upon the platelets.

The anti-sera may be either directly or indirectly labelled. It may be labelled for instance with a radioisotope, typically $^{125}I$, or it may be labelled with a conjugated enzyme which acts upon a substrate to produce a spectro-photometically detectable product. Rather than label the first antibody, it is also possible to label a second antibody directed against the first.

Following a brief incubation to allow antibody binding to occur, the excess antibody is washed off and the amount of bound label assayed. To reduce the amount of non-specifically bound anti-sera, the solution containing the antibody generally contains a non-labelled protein source such as bovine serum albumin or ovalbumin at concentrations of 0.2-0.8% (w/v).

This assay can be performed using either whole blood, or platelet rich plasma (PRP) with either Na citrate or EDTA as anticoagulant. Washed leucocytes, platelet fractions of blood can also be used. The assay system can be used to test serum of plasma from test animals by incubating the blood cells of non-pregnant animals with the serum or plasma from test animals (incubation period 10-60 mins). It is even possible to test the serum or plasma from a test subject from one species with platelets of another species. References herein to blood include reference to any platelet containing body fluid derived from whole blood.

It should be noted, however, that with each of the above alterations of the assay slightly different responses may result. The most important difference is that in the direct testing method (i.e. where whole blood of the test subject is used), the higher numbers of platelets in non-pregnant animals may result in a high number of bound platelets since there is a decreased platelet count in pregnant animals. This may occur even though the proportion of bound cells is smaller than with pregnant animals. For this reason there are advantages in testing a standard concentration of platelets. In the indirect assay on the other hand differences in adhesion represent true differences in the extend of platelet adhesion.

Platelet Aggregation

Unlike platelet adhesion, platelet aggregation is a calcium (i.e. multivalent ion) dependent event. Following the interaction of platelets with an appropriate stimuli (e.g. surfaces with a high critical surface tension or electropositive charge, proteolytic enzymes (e.g. thrombin), some prostaglandins and some macromolecules including collagen and insoluble immune complexes) the presence of calcium ions allows the biochemical events normally associated with platelet activation to occur. These changes include an irreversible shape change, release of granular material and the initiation of platelet aggregation:

There are a vast array of factors which have been shown to be stimulants for platelet activation and an equally vast array of factors which have been shown to either enhance or depress the response of platelets to these stimuli. In our studies it has been found that substances which cause differential platelet adhesion, e.g. glass, plastics (e.g. polystyrene) also result in differential platelet aggregation.

By exposing blood or PRP to glass and adding a small concentration of calcium ions, it is possible to distinguish between blood from pregnant and non-pregnant animals based upon the extent of platelet aggregation.

There are a number of ways to quantify platelet aggregation. The simplest way is to visualize the blood under a microscope with phase optics and compare the extent of platelet aggregation. The traditional way to quantify platelet aggregation is the spectro-photometric detection of the change in optical density of a solution containing platelets. It is also possible to monitor the release of excreted factors from platelet granules. This granular release is a consequence of platelet activation and aggregation. These factors include serotonin, Ca ions, Pyrophosphate, Acid hydrolases, Fibrinogen-Fibrin, Potassium, Platelet permeability factor, platelet Chemostatic factor, Platelet factor 4 (anti-heparin factor) heparin and albumin. Of these factors serotonin has been extensively described in the literature as a means of assessing platelet aggregation. This entails loading non-activated platelets with radioactively labelled serotonin and the subsequent monitoring of the extent of release of radiolabel following platelet activation.

A very useful method for observing platelet aggregation involves observing the extent of platelet-induced polystyrene latex particle aggregation. The advantages of this system are that:

(a) polystyrene particles have the physical characteristics that induce platelet adhesion in the absence of Ca ions (i.e. high critical surface tension, and net +ve charge), thus upon addition of Ca ions, polystyrene acts to cause platelet activation and aggregation, (b) since the platelets are adherent to the polystyrene particles, platelet aggregation results in latex aggregation. This aggregation can easily be seen with the naked eye.

To readily observe the differences between 'pregnant' and 'non-pregnant' platelet reactivity it is best to use conditions that will allow only minimal platelet activation in normal non-pregnant individuals. The easiest way to manipulate this condition is by regulating the supply of Ca ions.

In mouse latex aggregation studies, blood was collected with 0.04% (W/V) EDTA. This was mixed with $CaCl_2$ to give a final Ca ion concentration of 5 mM. To 6 volumes of blood or PRP 1 volume of 10% latex particles suspension is added. This mixture is placed upon a slide (glass or plastic) and mixed. Under these conditions there is little if any visible aggregation of latex particles. Blood from pregnant animals, on the other hand, shows a significant degree of aggregation at these calcium ion levels.

For other mammal species and perhaps even with various strains of some species, the conditions may need to be optimised to provide the greatest differentiation between 'pregnant' and 'non-pregnant' blood samples.

Latex particles having a diameter in the range 0.1 to 1.0 micrometers have proved satisfactory.

A difficulty that has been shown to arise with the use of latex particles for monitoring platelet aggregation, is the incidence of non-specific aggregation. We have found that in some species, particularly the horse, high levels of circulating gonadotrophins in serum or plasma can result in non-specific aggregation of polystyrene particles. This aggregation can disguise the effects of platelet aggregation. This non-specific aggregation can be readily identified since it is based upon adhesion due to static electricity and is therefore readily disassociatable. Polystyrene aggregation due to platelet aggregation, on the other hand, is non-disassociatable. This non-specific polystyrene aggregation can be reduced to some extent by inclusion of non-polymeric charged moieties in the reaction mixture. It is advisable, however, that where such non-specific aggregation does occur (e.g. due to oestrus and after day 30 of pregnancy in the mare) that other methods (e.g. serotonin release) be used.

Another type of method for quantifying the rate and extent of platelet activation is based upon the ability of electropositive surfaces to initiate platelet adhesion and aggregation. In the presence of Ca ions platelet aggregation occurs and this results in a build up of platelets around the electrode can be monitored by:

(1) visual observation, using microscope, or
(2) measuring the increase in impedance to the current flow which results from platelet build-up to the electrode surface. Careful control of the conditions, e.g. current flow and Ca ion concentration, results in a minimal platelet aggregation in blood of non-pregnant individuals while there is a significant aggregation with pregnant individuals.

Inhibitor Studies

A general increase in platelet reactivity cannot necessarily be considered a pregnancy-specific response. Similar changes may also occur during some infectous diseases, inflammatory cologically active agents will also affect platelet reactivity and hence affect pregnancy diagnosis.

To overcome this problem there is an advantage to test subjects both before and after suspected conception. In this way an assessment in the relative changes in platelet reactivity can be gained.

It is also possible to minimize this possibility of non-pregnancy specific aggregation by the use of inhibitors to various activating stimuli which are unrelated to pregnancy.

Using the latex agglutination assay with mice, we have shown that the combination of the following substances with the latex suspension can reduce the risk of non-specific platelet activation without affecting pregnancy diagnosis significantly.

(1) Heparin—this prevents both the generation and activity of thrombin,
(2) anti thrombin III, this also prevents the generation and action of thrombin,
(3) acetyl salicylic-acid, this inhibits the generation of prostaglandins, some of which can cause platelet activation,
(4) Indomethacin, inhibitor of prostaglandin generation,
(5) combination of pyruvate kinase and phosphoenal pyruvute, this catalyses the conversion of Adenosine di-phosphate (ADP) to Adenosine Tri-phosphate (ATP). ADP is a potent stimulant of platelet activation, and
(6) Adenosine, this swamps the concentration of ADP present thereby inhibiting its effects.

The inclusion of these inhibitors prevents or minimises platelet activation by the three major groups of platelet activators, i.e.

(1) proteases—particularly thrombin
(2) prostaglandins
(3) ADP

The inclusion of other inhibitors can exclude non-specific activation by other factors, e.g. we might include inhibitors of proteases other than serine proteases. It is also possible to pretreat test serum/plasma to remove factors that may cause non-specific platelet activation. Such non-specific factors might include anti-platelet antibodies or insoluble immune complexes. These factors could be removed by prior treatment of the test fluid with a solid phase immunoabsorbent.

Examples of the invention will now be described.

PLATELET ACTIVATION

Example 1 (Platelet adhesion)

Direct Assay of Platelets from pregnant animals

1. A sample of blood (0.25-1 ml) is collected into an equal volume of Alsevers solution (Alsevers solution is an anticoagulant containing Na citrate).
2. Platelets are separated from other blood cells by density gradient centrifugation. The gradient used is a Ficoll-paque (Pharmacia Pty. Ltd.). Separation is achieved by carefully layering the blood sample over half the blood volume of Ficoll in plastic centrifuge tubes. This blood sample is centrifuged at low speed (100-400 g) for any period of time over ten minutes. Following centrifugation the platelets form a distinct layer of cells above the ficoll meniscus.
3. The cells are harvested and placed into a glass centrifuge tube. They are then washed thrice with an isotonic medium (e.g. Phosphate buffer saline, PBS) and then resuspended with PBS to the original volume of blood. In the presence of the glass surface, the thrombocytes become fully activated. The thrombocytes are left for a period of time (8-15 mins) for the activation to occur and the extent of adhesion of the platelets can be examined by any number of methods known to the skilled man. The most convenient method is to simply examine the platelets with phase contrast microscopy.
4. Extensive platelet activation indicates pregnancy.

Example 2 (Platelet adhesion)

Indirect assay of platelets

This method allows the assessment of pregnancy by using body fluids from the test animal only.

Platelets from a non-pregnant animal are incubated with sera as plasma from test animal for a period of time (0.5-1 hour). Then serum is washed by centrifugation and the platelets examined for activation as above.

SYSTEMS FOR PREGNANCY DIAGNOSIS

Example 3 (Platelet aggregation)

A system based upon the differential agglutination of platelets from pregnant and non-pregnant animals by (polystyrene) particles contains:

(a) Polystyrene latex suspension, the polystyrene particles typically have a diameter of 0.2 μm-1 μm. The suspension might have a concentration of 2-15% (w/v).

(b) An anticoagulant solution containing sufficient ethylenediaminetetra-acetic acid di-sodium salt (EDTA) to prevent all blood coagulation and platelet activation. It would also be possible to use Na citrate as the anticoagulant. Heparin however is unsuitable here.

(c) An aqueous solution of $CaCl_2$ containing sufficient Ca ions to allow platelet activation to occur in blood of pregnant animals but not non-pregnant animals.

(d) A solution of inhibitory substances designed to prevent non-specific activation of platelets. Typically this solution might contain 100 i.u./ml heparin, 1.5 mM acetyl salicylic acid, 0.05 adenosine. Other inhibitors can be included to combat specific sources of non-specific aggregation.

(e) The kit might also contain for comparison, fluid samples that are known to give (i) +ve pregnant result, (ii) −ve pregnancy result, and (f) A further control to provide inhibition of the pregnancy response, i.e. −ve control. The addition of a small volume of a 1% solution of protamine sulphate is sufficient to abolish pregnancy induced latex agglutination.

Example 4 (Platelet adhesion)

A suitable system contains:

(a) a suitable surface for platelet adhesion. This might take the form of glass or plastic centrifuge tube or individual tests, or plastic microfitre plates for large scale analysis.

(b) a physiological solution for washing off non-adherent cells.

(c) A fixative, to fix adherent cells to surface, e.g. 80% ethanol, 80% methanol, formaldahyde, gluteraldahyde.

(d) A solution containing a macromolecule source (e.g. albumin) to prevent non-specific binding of antibody to surface, and (e) An appropriately labelled antibody or other probe to detect the presence of adherent cells.

Similar kits might also be provided for methods such as serotonin release by platelets. It will also be possible to provide a device for measuring the build-up of platelets to electropositive electrodes thus giving a quantifiable means of pregnancy diagnosis.

Test Results

1. Latex Aggregation Test—mice, Direct

Method: 0.25 ml of blood was collected from periorbital plesus placed into 10 μl of 3% EDTA and mixed. Either whole blood or PRP can be used in assay. 12 μl of blood is mixed with 2 microliters of a 10% solution of 0.8 μm diameter polystyrene particles together with 2 μl of 30 mM $CaCl_2$;

Two μl of 1000 i.u./ml heparin, 2 μl of 1.5 mM aspirin can be added as options to prevent non-specific aggregation.

These solutions are placed together with a slide and mixed by rotating the slide. With blood from pregnant animals extensive aggregation occurs within 5-10 secs.

The extent of aggregation was graded 0,-4.

0 representing no aggregation 4 representing maximum aggregation. The results are given in Table 1. Non-pregnant animals always showed an aggregation of 0-1 while pregnant (day 1-8) showed a response of 3-4.

TABLE 1

| Animal (strain and treatment) | | Samples | Result |
|---|---|---|---|
| OS female mice | | | |
| *random stages of the oestreuscycle | | 55 | 0-1 |
| *oestrus 5 | | 1 | |
| *immature, prepubertal | | 7 | 0 |
| *multiparous non-pregnant | | 4 | 0-1 |
| *48 post pregnant mare serum gonadotrophin injection | | 3 | 0-1 |
| *12 h post human chorionic gonadotrophin injection | | 2 | 1 |
| *after mating with vasectomized males | 6 h | 1 | 0 |
| | 12 h | 2 | 0 |
| | Day 2 | 2 | 0 |
| | Day 3 | 2 | 0 |
| | Day 4 | 2 | 0 |
| | Day 6 | 2 | 0 |
| *bilateral tubal ligation followed by normal mating | 6 h | 1 | 0 |
| | 12 h | 1 | 0 |
| | 24 h | 1 | 0 |
| *natural ovulation and normal mating | 6 h | 4 | 1 |

TABLE 1-continued

| Animal (strain and treatment) | | Samples | Result |
|---|---|---|---|
| | 12 h | 5 | 1–3 |
| | 18 h | 7 | 3–4 |
| | Day 2 | 20 | 3–4 |
| | Day 3 | 24 | 4 |
| | Day 4 | 13 | 3–4 |
| | Day 5 | 32 | 4 |
| | Day 6 | 20 | 3–4 |
| | Day 7 | 6 | 3–4 |
| | Day 8 | 7 | 2 |
| | Day 9 | 5 | 1–2 |
| OS mature males | | 12 | 0–1 |
| OS mature female with lymphoma (Cancer) | | 2 | 0 |
| CBA strain | | | |
| *non-pregnant females | | 5 | 0 |
| *pregnant females | D1 18 ppc | 2 | 3 |
| | D3 | 4 | 3–4 |
| | D4 | 2 | 3–4 |
| C5761/6 strain | | | |
| *non-pregnant female | | 4 | 0–1 |
| *male | | 2 | 0–1 |
| *pregnant female | D2 | 4 | 4 |
| | D4 | 5 | 4 |

2. Double Blind Trial: Latex Aggregation Test

A double blind trial using the same method as described above was carried out. This trial involved one person selecting 40 OS mice:

20 pregnant OS females (Day 1–7)
10 non-pregnant—random stages of the oestrous cycle
5 pseudopregnant
5 mature males Each animal was number coded and given to a second person for pregnancy diagnosis. Following diagnosis, the code was broken and success of diagnostic procedure determined. It was found that using this test system with mice there was a 100% success rate in diagnosis of pregnancy. There were no false positives or false negatives.

3. Latex Aggregation Test: mice, cow, horse and human-indirect

This procedure used the same conditions as for the direct assay. The main difference is that it requires the collection of either platelets or total cell pellet from an animal and the resuspension of these cells with plasma from test animals.

Upon resuspension the platelet reactivity can be tested immediately. We have found that this assay is much superior using EDTA plasma or heparin-plasma than serum.

The results are given in Tables II and III.

TABLE II

| Platelet Cell Source (Mice) | Test Fluid | Samples | Result |
|---|---|---|---|
| OS non-preg female Platelet pellet | *EDTA plasma OS non-pregnant female | 20 | 0–1 |
| | *EDTA Plasmas OS male | 4 | 0 |
| | *EDTA plasma pseudopregnant OS D2-4 | 7 | 0 |
| | *EDTA plasma preg female D1 6 h | 2 | 0 |
| | 12 h | 3 | 2–3 |
| | EDTA plasma pregnant OS female | | |
| | 18 h | 3 | 4 |
| | Day 2 | 8 | 4 |
| | Day 3 | 7 | 4 |
| | Day 4 | 7 | 4 |
| | Day 5 | 6 | 3–4 |
| | Day 6 | 5 | 4 |
| OS non-female | EDTA plasma non-preg OS female | 12 | 0–1 |
| | EDTA plasma pseudopregnant preg D2-4 | 5 | 0–1 |
| | EDTA plasma preg OS. | | |
| | D1 18 h | 2 | 3 |
| | Day 2 | 3 | 3–4 |
| | Day 3 | 4 | 4 |
| | Day 4 | 6 | 4 |
| | Day 5 | 7 | 3–4 |
| | EDTA plasma C5761/6 non-preg | 2 | 0–1 |
| | EDTA plasma C5761/6 preg D2-4 | 5 | 3–4 |
| | EDTA plasma C5761/6 male | 2 | 0 |
| | Heparin plasma OS fem. non-preg | 3 | 0–1 |
| | Heparin plasma OS fem. preg D2-4 | 6 | 3–4 |
| OS pregnant white cell fraction | EDTA plasma OS non-pregnant | 4 | 0–1 |
| | EDTA plasma OS preg D2-4 | 4 | 3–4 |

Note this last experiment shows that the changes in the platelet reactivity really do depend and are elicited by a plasma factor

TABLE III

Indirect latex test of cow, horse and human plasma

| Platelet Cell Source | Test Fluid | Samples | Result |
|---|---|---|---|
| Gelding whole cell fraction | EDTA plasma non-preg. mare | 6 | 0–1 |
| | EDTA plasma from gelding | 2 | 0 |
| | EDTA plasma from mares after service | | |
| | Day 2 | 4 | 3 mares–2 1 mare–1 |
| | Day 6 | 3 | 2–3 |
| | Day 12 | 3 | 2–3 |
| | Day 18 | 5 | 2–3 |
| male human platelet pellet | non-pregnant female human | 4 | 0–1 |
| | normal human male | 5 | 0–1 |
| | 4 wk preg human EDTA plasma | 1 | 2 |
| | 6 wk preg human EDTA plasma | 1 | 3 |
| | 8 wk preg human EDTA plasma | 1 | 2–3 |
| Cow whole cell fraction | EDTA plasma from non-preg. cow | 4 | 0–1 |
| | EDTA plasma-bull | 2 | 0–1 |
| | EDTA plasma-heifers following artificial insemination | | |
| | 18 h | 6 | 0–1 |
| | Day 3 | 5 | 3 heifer–2 2 heifer–0 |
| | Day 6 | 3 | 2–3 |
| | Day 10 | 3 | 2–3 |

We claim:

1. A method of detecting pregnancy in a mammal at an early stage shortly following conception which comprises detecting enhanced activation of blood platelets.

2. A method according to claim 1 which comprises monitoring of platelet aggregation on an electropositive electrode in the presence of multivalent ions.

3. A method according to claim 1 wherein the platelet activation is detected in the presence of an inhibitor for preventing non-pregnancy-specific activation.

4. A method according to claim 3 wherein the inhibitor prevents non-pregnancy-specific activation by an activator selected from the group consisting of proteases, prostaglandins and adenosine diphosphate.

5. A method according to claim 3 wherein the inhibitor is selected from the group consisting of heparin, anti-thrombin, acetyl salicylic acid, indomethacin, a combination of pyruvate kinase and phosphoenol pyruvate, and adenosine.

6. A method according to claim 1, which comprises detecting enhanced platelet adhesion to a substrate.

7. A method according to claim 6 which comprises exposing a blood sample containing an anticoagulant to the substrate and detecting the extent of reduction of the platelet count in the sample; a relatively large reduction indicating enhanced platelet adhesion.

8. A method according to claim 6 which comprises exposing a blood sample containing an anticoagulant to the substrate and detecting the number of platelets adhering to the substrate; a relatively large number of adherent platelets indicating enhanced platelet adhesion.

9. A method according to claim 1, which comprises detecting enhanced aggregation of the platelets in the presence of a multivalent ion.

10. A method according to claim 9 wherein the platelet aggregation is monitored by:
 (i) direct observation using a microscope with phase optics,
 (ii) spectrophotometric densitometry, or
 (iii) detection of the release of excretal factors from platelet granules.

11. A method according to claim 9 wherein the platelet aggregation is monitored by means of the aggregation of a polystyrene latex, which comprises contacting the blood and an anticoagulant with a polystyrene latex suspension in the presence of multivalent ions and an inhibitor for preventing non-pregnancy-specific platelet activation.

12. A system for detecting pregnancy in a mammal at an early stage by latex agglutination which comprises:
 (a) a polystyrene latex suspension,
 (b) an anticoagulant,
 (c) a source of multivalent ions, and
 (d) an inhibitor for preventing non-pregnancy-specific platelet activation.

13. A system according to claim 12 wherein the latex particles have a diameter of 0.1 to 1.0 micrometers and a concentration of 2–15% weight to volume.

14. A system according to claim 12 wherein the inhibitor comprises 100 iu/ml heparin, 1.5 mM acetyl salicylic acid and 0.05 mM adenosine.

15. A system for detecting pregnancy in a mammal at an early stage by platelet adhesion, which comprises:
 (a) a substrate of a glass or plastics material,
 (b) a fixative for fixing adherent platelets to the substrate,
 (c) a labelled antibody to detect the presence of platelets adhering to the substrate, and
 (d) a macromolecular source to prevent non-pregnancy specific binding to the substrate.

* * * * *